(12) United States Patent
Ozbal et al.

(10) Patent No.: US 6,812,030 B2
(45) Date of Patent: Nov. 2, 2004

(54) SYSTEM AND METHOD FOR HIGH THROUGHPUT SAMPLE PREPARATION AND ANALYSIS USING COLUMN CHROMATOGRAPHY

(75) Inventors: Can Ozbal, Cambridge, MA (US); Ian W. Hunter, Lincoln, MA (US); John Linton, Lincoln, MA (US)

(73) Assignee: BioTrove, Inc., Cambridge, MA (US)

( * ) Notice: Subject to any disclaimer, the term of this patent is extended or adjusted under 35 U.S.C. 154(b) by 472 days.

(21) Appl. No.: 09/893,311

(22) Filed: Jun. 27, 2001

(65) Prior Publication Data

US 2002/0160521 A1 Oct. 31, 2002

Related U.S. Application Data

(63) Continuation-in-part of application No. 09/842,361, filed on Apr. 25, 2001.

(51) Int. Cl.[7] .................................................. B01D 15/08
(52) U.S. Cl. ............................. 436/50; 436/161; 422/63; 422/70; 210/656; 73/61.56
(58) Field of Search ............................. 210/656, 659, 210/198.2; 73/61.52, 61.56; 436/50, 161; 422/63–67, 70

(56) References Cited

U.S. PATENT DOCUMENTS

| | | | |
|---|---|---|---|
| 3,566,677 A | 3/1971 | Cole et al. ............ 73/61.3 |
| 3,734,622 A | 5/1973 | Adler ................... 356/103 |
| 4,071,315 A | 1/1978 | Chateau ................. 23/230 |
| 4,111,553 A | 9/1978 | Garnys ................. 356/36 |
| 4,659,677 A | 4/1987 | Glover et al. ........... 436/174 |
| 4,837,160 A | 6/1989 | Meserol et al. .......... 436/174 |
| 4,841,145 A | 6/1989 | Wada et al. ............ 250/304 |
| 4,883,642 A | 11/1989 | Bisconte ............... 422/66 |
| 5,006,749 A | 4/1991 | White .................. 310/323 |
| 5,191,212 A | 3/1993 | Falk et al. ............. 250/288 |
| 5,334,837 A | 8/1994 | Ikeda et al. ............ 250/339 |
| 5,486,337 A | 1/1996 | Ohkawa ................ 422/100 |
| 5,508,200 A | 4/1996 | Tiffany et al. ........... 436/44 |
| 5,516,692 A | 5/1996 | Berndt ................. 435/286.7 |
| 5,630,943 A * | 5/1997 | Grill ................... 210/659 |
| 5,906,223 A | 5/1999 | Pinkham ............... 137/597 |
| 6,019,897 A | 2/2000 | Horsman et al. ......... 210/198.2 |
| 6,066,848 A | 5/2000 | Kassel et al. ........... 250/288 |
| 6,296,771 B1 * | 10/2001 | Miroslav ............... 210/656 |
| 6,318,157 B1 * | 11/2001 | Corso et al. ............ 73/61.52 |
| 6,344,172 B1 * | 2/2002 | Afeyan et al. .......... 422/70 |

FOREIGN PATENT DOCUMENTS

| | | | |
|---|---|---|---|
| EP | 60022478 | 4/1985 | ............ H02N/2/00 |
| EP | 0556748 A2 | 12/1993 | ............ G01N/15/14 |
| EP | 0752281 A2 | 5/1996 | ............ B07C/5/36 |
| EP | 0 983 788 A2 | 3/2000 | ............ B01F/13/00 |
| FR | 2 820 058 | 8/2002 | ............ B01L/3/00 |
| WO | WO9534374 | 12/1995 | ............ G01N/21/86 |
| WO | WO9808093 | 2/1998 | ............ G01N/33/543 |
| WO | WO9815355 | 4/1998 | |
| WO | WO 99/11373 | 3/1999 | ............ B01L/3/02 |
| WO | WO 00/45929 | 8/2000 | ............ B01D/15/08 |
| WO | WO 00/63705 | 10/2000 | ............ G01N/35/00 |

* cited by examiner

*Primary Examiner*—Jeffrey Snay
(74) *Attorney, Agent, or Firm*—Bromberg & Sunstein LLP

(57) ABSTRACT

A system and method high throughput sample preparation and analysis using column chromatography. Each port in a plurality of ports has a port input that interfaces with a first fluid source and a port output. A fluidic circuit is coupled to each port output and to a second fluid source, the fluidic circuit for controlling fluid flow from the plurality of ports and the second fluid source. The fluidic circuit is also coupled to a plurality of chromatography columns. An interface to an analyzer receives output from at least one of the plurality of chromatography columns. The plurality of chromatography columns is moved relative to the analyzer via a translation stage, such that sample output from one of the plurality of chromatography columns can be selectively presented to the analyzer.

31 Claims, 4 Drawing Sheets

SYSTEM AND METHOD FOR HIGH THROUGHPUT SAMPLE PREPARATION AND ANALYSIS USING COLUMN CHROMATOGRAPHY

PRIORITY

This application is a continuation-in-part of U.S. patent application Ser. No. 09/842,361, filed Apr. 25, 2001, entitled "System and Method for High Throughput Processing of Droplets," which is hereby incorporated by reference, in its entirety.

TECHNICAL FIELD

The present invention pertains to a system and method for high throughput sample preparation using column chromatography, followed by analysis of the samples, where the analysis may include mass spectrometry and optical interrogation, such as fluorescence spectrometry, Raman spectroscopy, and UV absorption.

BACKGROUND OF THE INVENTION

High-throughput screening (HTS) is a method for the rapid and accurate analysis of large numbers of chemical compounds for activity against selected targets. Typical chemical libraries contain hundreds of thousands to millions of separate compounds that are screened against a wide variety of targets. The large numbers of compounds that must be routinely screened has led to a requirement for new technologies capable of rapid and quantitative analysis.

Various types of analysis performed on samples are enhanced by first preparing the sample. In particular, mass spectrometry is a powerful technique uniquely suited for many HTS applications. Mass spectrometry allows accurate quantification of a compound based on its mass alone, eliminating the need for the development of specific spectroscopic assays. The current state-of-the-art mass spectrometers using atmospheric pressure ionization (API) interfaces are not compatible with samples in solutions that contain high levels of non-volatile salts or contaminants. Non-volatiles in the sample can cause both suppression of the desired sample signal and can cause the mass spectrometer to fail due to build-up of precipitates within the ion guide and inlet. Therefore, samples must be purified from non-volatile contaminants and desalted prior to analysis. Additionally, this must be performed, as discussed above, in a manner conducive to high throughput screening.

SUMMARY OF THE INVENTION

A system for high throughput sample preparation and analysis using column chromatography is presented. The system includes a plurality of ports, each port having both a port input that interfaces with a first fluid source and a port output. A fluidic circuit is coupled to each port output and to a second fluid source, the fluidic circuit for controlling fluid flow from the plurality of ports and the second fluid source. The fluidic circuit is also coupled to a plurality of chromatography columns. An interface to an analyzer is provided that receives output from at least one of the plurality of chromatography columns. A translation stage allows for movement of the plurality of chromatography columns relative to the analyzer, such that sample output from one of the plurality of chromatography columns can be selectively presented to the analyzer.

In related embodiments of the invention, the system may include a plurality of syringes, each syringe for aspirating a sample to be analyzed and for acting as the first fluid source for one of the plurality of ports. The plurality of syringes may be in fixed positions relative to each other. For example, the plurality of syringes can be positioned in a linear array with 9 millimeter spacing between each of the syringes. The plurality of syringes may interface with the plurality of ports in a parallel manner. The plurality of syringes may be controlled by a controller, the controller comprising at least one device from the group of devices consisting of a robot, a translational stage, and a computer. Each port may include a compression fitting for interfacing with one of the plurality of syringes. The system may include a washing station for cleaning the array of syringes.

In other related embodiments of the invention, the sample to be analyzed may be located on a movable surface. The movable surface may be a fiber, laminate, web, or belt. The first fluid source may include a plurality of tubes, each tube for interfacing with one of the plurality of ports.

In still other related embodiments of the invention, the fluidic circuit includes a plurality of valves, each valve controlling fluid flow from the port output of one of the plurality of ports. A plurality of tee unions are provided, each tee union coupled to one of the plurality of valves and at least one chromatography column. A pump pumps fluid from a second fluid source, and at least one selection valve selectively couples an output from the pump to at least one of the plurality of tee unions. At least one of the plurality of valves may be an actively controlled shutoff valve or a passive check valve.

In yet other related embodiments of the invention, the interface may include a plurality of electrospray ionization sprayer tubes for interfacing with a mass spectrometer; each electrospray ionization sprayer tube coupled to one of the chromatography columns. The plurality of chromatography columns may be in fixed positions relative to each other, and may be positioned in a fixed linear array.

In another embodiment of the invention, a method for high throughput sample preparation and analysis using column chromatography is presented. A plurality of ports is interfaced with a first fluid source, each port having both a port input coupled to the first fluid source and a port output. Fluid flow is controlled from each port output and a second fluid source to a plurality of chromatography columns. The plurality of chromatography columns is moved relative to the analyzer, such that sample output from one of the plurality of chromatography columns can be selectively presented to the analyzer.

In related embodiments of the invention, the method may further include aspirating samples into a plurality of syringes, and interfacing the plurality of syringes with the plurality of ports. The syringes may be controlled using at least one device from the group of devices consisting of a robot, a translational stage, and a computer. The syringes may be cleaned at a washing station prior to aspirating samples.

In a related embodiment of the invention, the control of fluid flow from each port output and a second fluid source to a plurality of chromatography columns includes a plurality of valves that regulate fluid flow from the port output of each of the plurality of valves to a plurality of tee valves, each tee valve being coupled to at least one of the plurality of chromatography columns. Fluid is selectively pumped from the second fluid source to at least one of the plurality of tee valves.

In yet other related embodiments of the invention, the method further includes presenting sample from one of the plurality of chromatography columns to a mass spectrometer using an electrospray ionization sprayer tube. Undesired components may be blocked from entering the mass spectrometer by removing the voltage applied to the electrospray ionization sprayer tube, or by moving the electrospray ionization sprayer tube to a position in which the spray is physically blocked from entering the mass spectrometer.

In still other related embodiments of the invention, the method further includes performing at least one operation from the group of operations consisting of optical interrogation and mass spectrometry. Optical interrogation may include at least one of flouresence spectrometry, Raman spectrometry, and UV absorption. Controlling fluid flow may include delivering samples and wash from one of the plurality of ports to one of the plurality of chromatography columns in one substantially continuous action. Sample output may be selectively presented to the analyzer once every specified time period.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Figure 1:
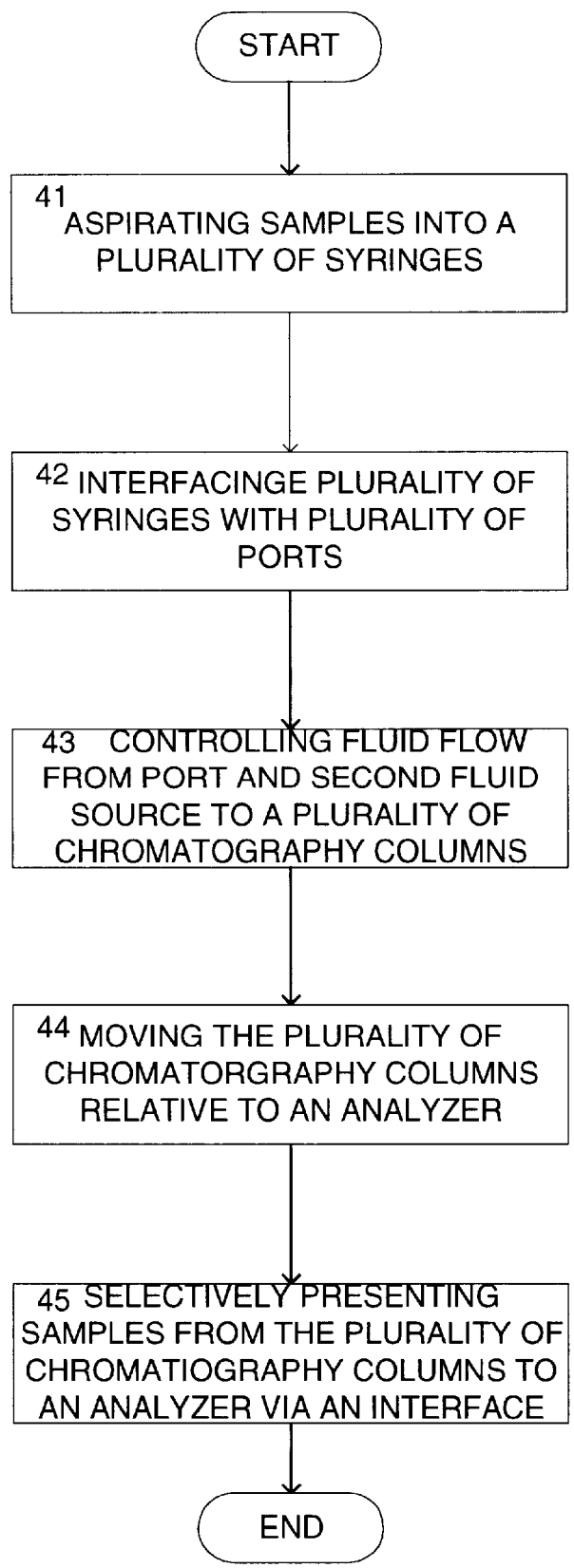
FIG. 1 is a flow chart depicting a method for high throughput sample preparation and analysis in accordance with one embodiment of the invention.

A system and method for high throughput sample preparation and analysis using column chromatography is presented. Referring to the flow chart of FIG. 1, which shows a method for high throughput sample preparation and analysis in accordance with one embodiment of the invention, a number of samples are aspirated into one, or in preferred embodiments, a plurality of syringes or tubes, step 41. The syringes or tubes are then interfaced with a plurality of port(s), step 42. A fluidic circuit controls fluid flow from both the port(s) and a second fluid source, which in preferred embodiments may be wash buffer or solvent, to a plurality of chromatography column(s), step 43. By controlling the fluid flow of samples and/or wash buffer into the chromatography column(s), the sample is prepared for analysis. The position of the chromatography column(s) is controllable via a translation stage, step 44. This allows the samples to be selectively presented, via an interface, to an analyzer, which may be a mass spectrometer for example, step 45. The system is capable of preparing large number of samples for analysis at a rate compatible for high throughput screening.

Sample preparation using column chromatography may include, but is not limited to, purification and desalting, and can be accomplished using well-established techniques familiar to those skilled in the art. The columns in the array are packed with a non-soluble gel, matrix, polymer, or particles (the column packing) with a desired surface chemistry. A vast number of packing chemistries are available and are familiar to those skilled in the art. Column arrays may be loaded uniformly with a given column packing or different column packings can be loaded into each member of an array of columns. The principle of chromatography relies on the differential affinity of the individual components in a complex mixture for the packing material. Typically, a sample is loaded onto a column for which it has an affinity. The column is washed with a buffer or solvent that elutes the undesired contaminants/salts off of the column while retaining the sample(s) of interest. The purified sample is then eluted off of the column with a second buffer or solvent for which it has a higher affinity for than the column packing material. Another type of chromatography relies on separation/purification of components in a complex mixture based on the relative size of the components. Common forms of chromatography that can be performed with this device include, but are not limited to, reversed phase, ion-exchange, immunoaffinity, size-exclusion, and gel filtration.

Figure 2:
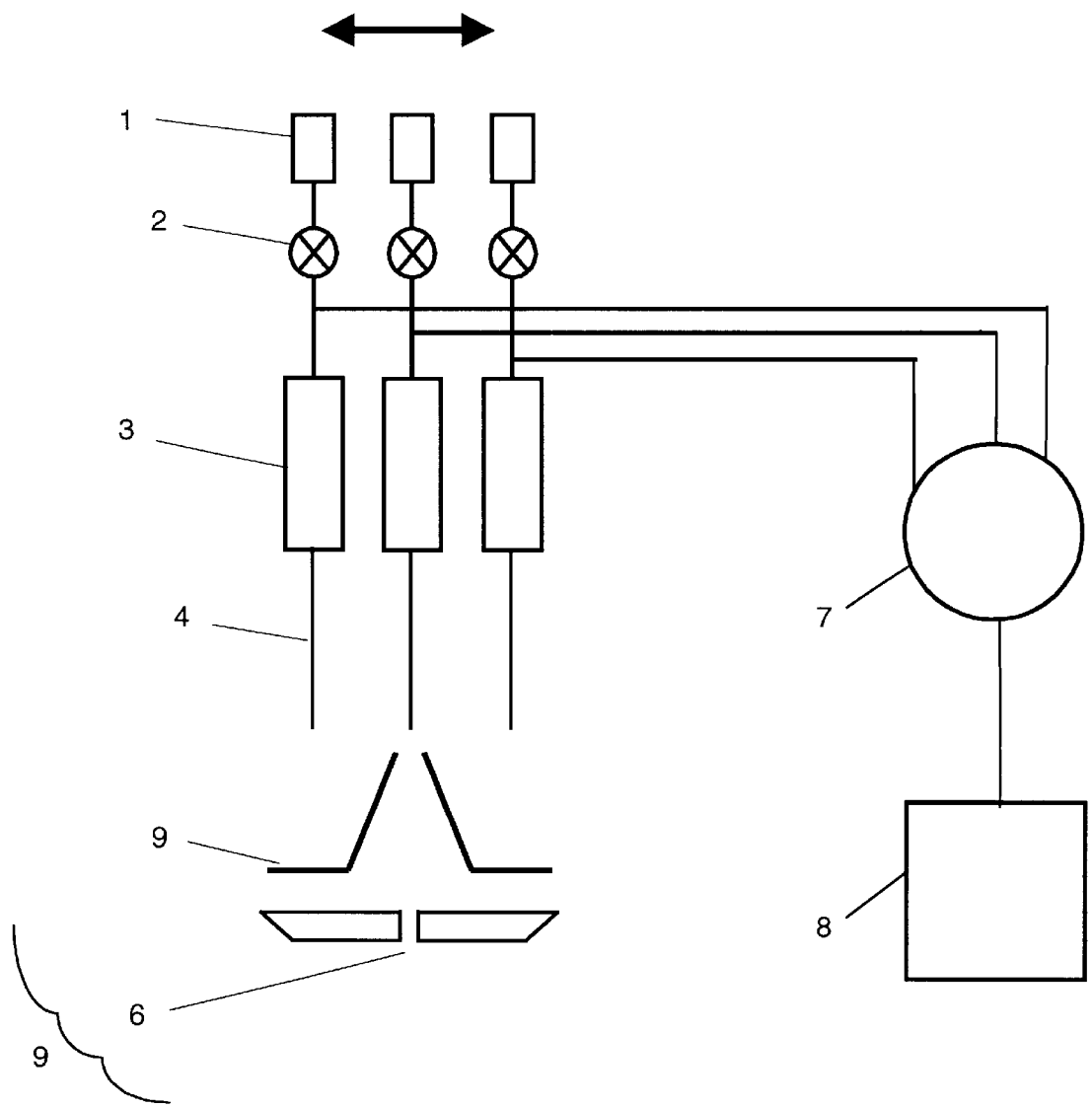
FIG. 2 is a schematic diagram of a system for high throughput sample preparation and analysis in accordance with one embodiment of the invention.

In accordance with one embodiment of the invention, FIG. 2 is a schematic diagram of a system 10 for high throughput sample preparation and analysis in accordance with one embodiment of the invention. A plurality of ports 1 interface with a first fluid source. The first fluid source may include a plurality of syringes or tubes (hereinafter referred to as syringes). In various embodiments of the invention, the needles of the array of syringes are coupled to the array of chromatography columns 3 through compression fitting in ports 1. The compression fitting forms a fluid tight seal around the needles of the syringes.

Plurality of ports 1 are coupled to a fluidic circuit which controls fluid flow to the chromatography columns. In various embodiments of the invention, the fluidic circuit may include a valve 2 placed between each port 1 and chromatography column 3 in the array. Valve 2 can either be an actively controlled shutoff valve or a passive check valve that limits the flow only from the ports 1 to the columns 3. The fluidic circuit may also contain a tee union 11 between valve 1 and chromatography columns 3 of the array from which elution and wash buffers or solvents can be added to each of the chromatography columns 3 in the array from a pumping system 8. A second valve(s) 7 controls flow from the pumping system to a particular chromatography column (s). Valve(s) 7 may be, for example, a single selection valve or alternatively, may consist of a plurality of valves, with each valve 7 controlling flow to one of the plurality of chromatography columns 3.

The eluate of each of the columns 3 in the array is channeled into an interface 4 for an analyzer. The analyzer may include, but is not limited to, optical interrogation and mass spectrometry. Types of optical interrogation that may be performed include fluorescence spectrometry, Raman spectrometry, or UV absorption. The interface 4 may include a simple tube attached to each column 3 so as to direct the fluid to the analyzer, or the interface may be more complex. For example, the eluate may be channeled into a thin metal tube onto which a voltage can be applied for direct atmospheric pressure electrospray ionization for use with a mass spectrometer.

The relative orientation between the interface and analyzer, such as between electrospray ionization sprayer 4 and inlet orifice of a mass spectrometer 6, can affect the performance of the analyzer. To minimize the inter-sample variation that is created by this effect, each column 3 and interface 4 in the array may be arranged and fixed into place in a linear arrangement and the entire array placed on a translation stage. The entire array is then moved relative to the entrance orifice 6 of the analyzer. In preferred embodiments, a constant distance and relative orientation between the interface 4 and the analyzer inlet orifice 6 is maintained for every sample. Alternatively, the eluate from each column 3 in the array could be diverted to a single interface through the use of a manifold. The manifold may be a potential source of contamination if improperly cleaned between each individual analysis. While it is possible to flush a manifold with solvents and/or buffers between each individual sample analysis for proper cleaning, this procedure typically takes time and limits the maximum rate at which samples can be analyzed.

In accordance with one embodiment of the invention, a number of samples is aspirated into one, or in preferred embodiments, a plurality of syringes. In a preferred embodiment, the syringes are in a fixed position relative to each other. The syringes may be positioned in a fixed linear array, such that they can interface with the ports in a parallel manner. Additionally, the syringes may be arranged with 9 millimeter spacing so as to facilitate transfer from standard 96 or 384 well microtiter plates.

Figure 3:
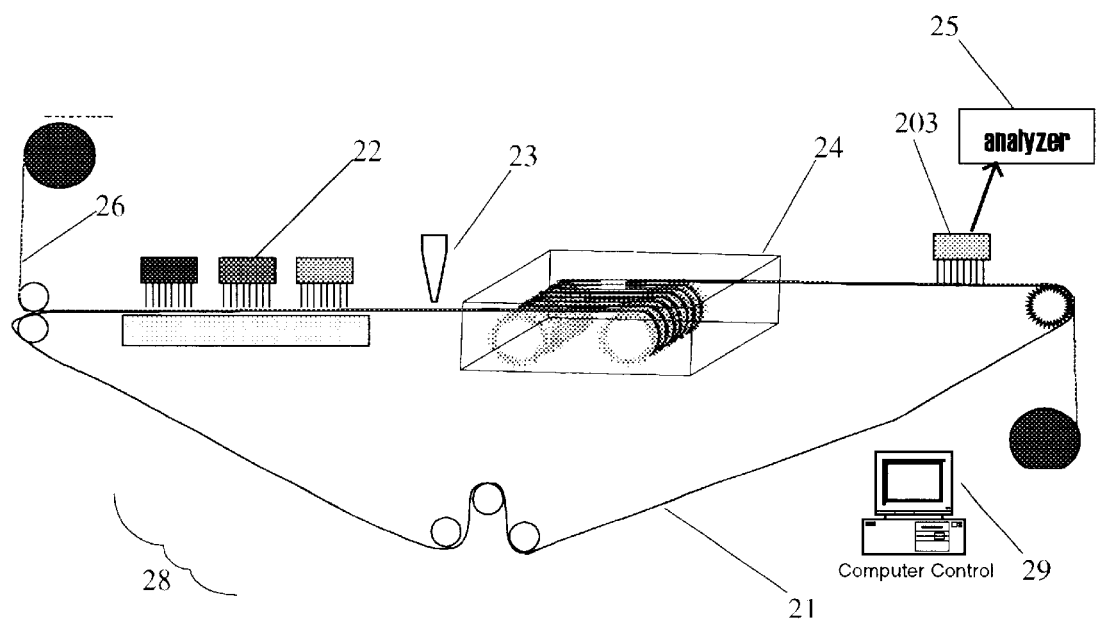
FIG. 3 is a schematic diagram of a system for high throughput sample preparation and analysis in accordance with one embodiment of the invention.

The samples to be aspirated may be located on a movable surface. In various embodiments, the movable surface may be a belt, such as a timing belt, or a fiber, as described in U.S. application Ser. No. 09/081,700, entitled "Apparatus and Method for Droplet Microchemistry", which is incorporated herein, by reference. The movable surface may be part of a system for high throughput processing of droplets/samples, as shown in FIG. 3. The system 28 may include, but is not limited to, a movable surface 21, a laminate 26 applied to the movable surface 26, a compound reformatter 22 which may also include a bank of syringes, a reagent addition station 23, an environmental delay chamber 24, computer control 29, and at least one analyzer 25, such as a mass spectrometer for example. The samples are aspirated off laminate 26 by plurality of syringes 203. Syringes 203 are then interfaced to chromatography columns 3 via ports 1, as shown in FIG. 2.

Figure 4:
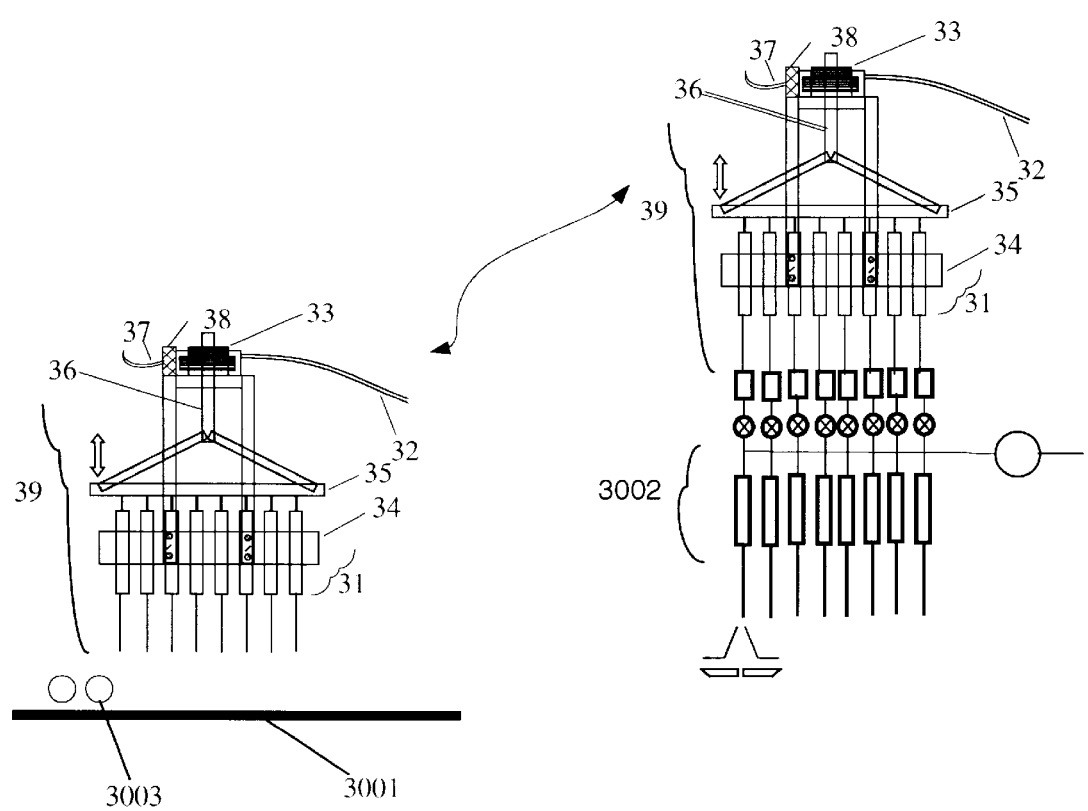
FIG. 4 is a schematic diagram of a translational stage for a bank of syringes in accordance with one embodiment of the invention.
Figure 2:
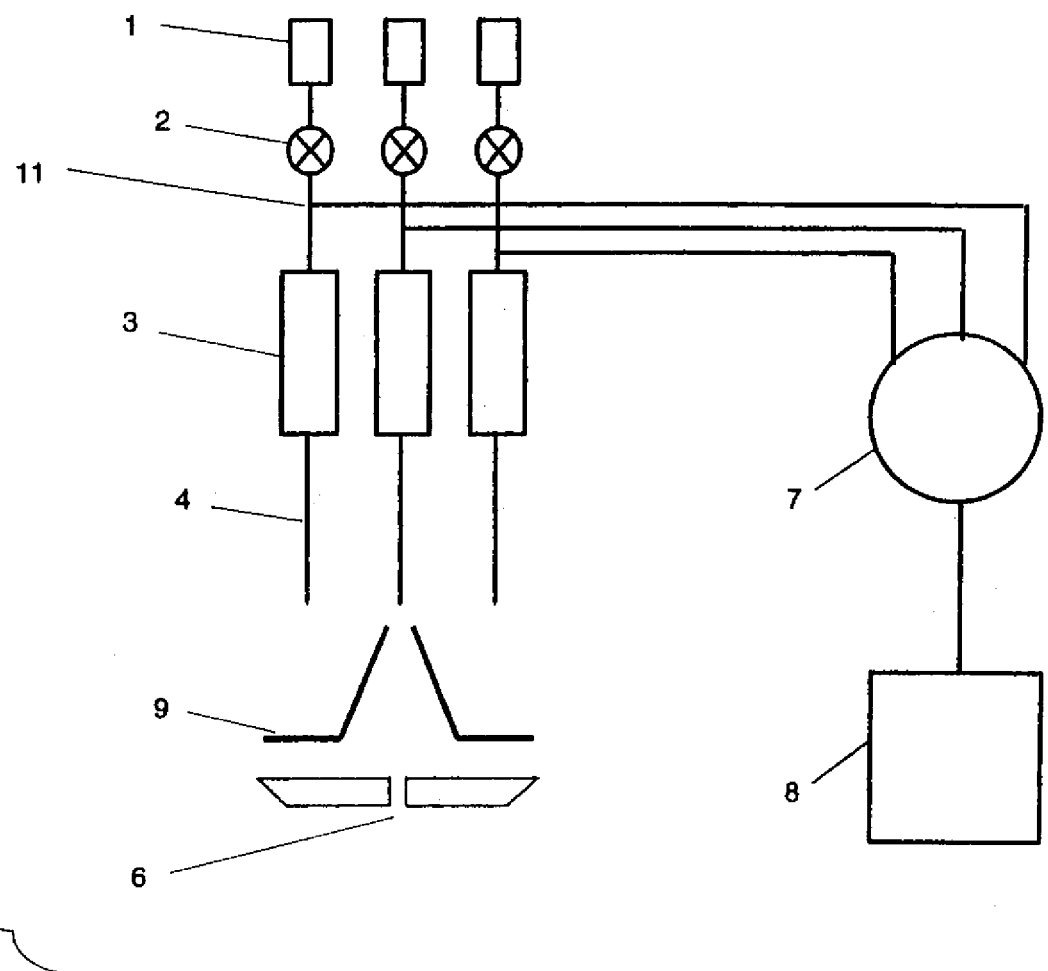

In preferred embodiments of the invention, the syringe(s) are controlled and accurately positioned in three-dimensional space and the plunger(s) of the syringe(s) moved with the use of translational stages, robotics, and/or computer control. FIG. 4 is a schematic diagram of a translational stage 39 that includes a bank of syringes 31, in accordance with one embodiment of the invention. Via translational stage 39, the bank of syringes may be moved between various stations, which include, but are not limited to a movable surface 3001 upon which samples 3003 can be aspirated, an array of chromatography columns 3002, a wash station, or a wash buffer station. Translational stage 39 may include a flexible coupling 32 or linkage that transmits torque to the plunger drive gear 33, allowing the torque source, which may be a stepper or servo motor, to be remotely mounted. This greatly reduces the mass of syringe bank assembly 34 when compared to a design that incorporates the motor on-board. Consequently, the overall assembly has little inertia relative to current designs and therefore requires less power to accelerate when attached to a positioning system. Greater accelerations can also be achieved for a given amount of applied force.

In various embodiments of the invention, a rack and pinion gearing 33 system is used to transform the rotary motion supplied to syringe bank 34 by the motor and coupling into a linear motion, which would then drive the syringe plungers in and out. Syringe plungers may be driven in combination with other plungers or may be driven independently. To combat backlash error a pair of racks attached to the plunger assembly 35 may be used. By mounting the rack gear pieces 36 slightly translated in the direction of their length with respect to each other backlash between drive pinion 33 and plunger rack 36 may be 'taken up' at assembly time.

An alternative gearing scheme could be incorporated such as a worm gear driving a threaded rod. Plunger bar 35 would be driven by either threading the rod through a part of the plunger assembly or rigidly attaching the threaded rod to plunger assembly 65 and threading the rod through the center of the worm gear. Either scheme requires mechanically constraining the plunger assembly to vertical translations. A worm gear configuration allows for a higher over all gear ratio to be achieved between drive system 33 and plunger assembly 34. It also has the virtue of being un-back drivable, that is, plunger assembly 34 would be self-locking and no torque would be required to hold the plunger assembly 34 in place.

In other embodiments of the invention, a rotary encoder 38 that is controlled externally 37 is attached to the drive gear axis 33 that drives the plunger assembly 34. By using rotary encoder 38, precise metering of the fluid can be achieved as it dispensed from the syringes.

Translational stage 32 is attached to a positioning system such that bank of syringes 31 are positioned to aspirate the samples 34 from the moving surface or laminate 32. After aspirating the samples 34, the bank of syringes are moved, for example, such that they interface with the plurality of ports 36, which are coupled via the fluidic circuit 38 to the chromatography columns 37. Samples 34 can then be processed and analyzed.

In accordance with one embodiment of the invention, prior to sample aspiration, a large reservoir of wash buffer or solvent is aspirated into the barrels of the array of syringes. The sample to be analyzed is separated from this reservoir with a small plug of air. A volume of sample is drawn into the array of syringes such that the sample is limited to the needles of the array of syringes. The syringes are then moved and docked into the compression fittings of the ports 1 (referring to FIG. 2) in the array of columns 3. Each valve 2 is opened and valve(s) 7 for the array of columns 3 is closed. The entire contents of the array of syringes are then expressed onto the array of columns 3 by simultaneously depressing the plungers of the array of syringes. The samples localized in the needles of the array of syringes are expressed onto the chromatography columns 3 and the impurities/salts are washed from the column with the wash buffer in the barrels of the syringes. The column array 3 is positioned at this time such that the wash buffer from none of the columns 3 is allowed to enter the inlet 6 of the mass spectrometer. After the contents of the syringes have been expressed valves 2 are closed. The array of syringes is then decoupled from the syringe port 1 compression fittings and is sequentially washed at a cleaning station, the barrels are filled with wash buffer or solvent and a plug of air and the next set of samples is aspirated.

To elute the samples off of the array of chromatography columns each valve 2 is closed. At this time the appropriate electrical voltage is applied to the metallic positioning jig that causes each of the electrospray needles 4 that make up the API mass spectrometry interface to become electrified. The sheath and/or shield gases used by the mass spectrometer interface are also applied. The column array 3 is moved via another translation stage, such that the first column in the array can be sprayed towards the inlet orifice of the mass spectrometer. Valve 7 for this single chromatography column within the array is selectively opened and elution buffer is selectively delivered to that single column in the array 3. The elution buffer causes the desalted and purified sample to be eluted from the selected column and into the inlet 6 of the mass spectrometer through the described API interface. The sample(s) within each chromatography column within the array 3 are individually analyzed by selectively delivering the elution buffer or solvent from the pumping system 8 to that column by opening valve 7 for the selected column only while keeping the valve closed for the other columns. The next sample is analyzed by moving the column array 3 using the translation stage such that the next column is allowed to spray into the inlet orifice 6 of the mass spectrometer and valve 7 is opened to allow for selective delivery of elution buffer or solvent to that column. A skimmer 9 is permanently positioned in front of the inlet orifice 6 of the mass spectrometer to ensure that residual spray from columns that have already been analyzed is excluded from entering the mass spectrometer. Once the samples within each column are analyzed the voltage applied to the metal tubes and, if applicable, the sheath and/or shield gasses of the API interface of the mass spectrometer are turned off and the column array 3 is moved to the initial position in which none of the columns can spray into the mass spectrometer. This stops the spraying of the samples into the mass spectrometer and protects the instrument from any undesirable contaminants and/or salts.

The chromatography columns in the array are then cleaned by opening valve(s) 7 and flushing each columns with an excess amount of elution buffer. The columns 3 can either be cleaned individually in serial or in a parallel fashion. Cleaned columns are similarly re-equilibrated with wash buffer or solvent also delivered by the pumping system 8. At this point the cycle is begun again and the next set of samples are delivered to the array of chromatography columns 3 from the array of syringes.

An example in accordance with one embodiment of the invention is provided below. The example is not intended to limit the scope of the invention. An enzyme inhibition assay was performed in a 96 well microtiter plate. Each well of the 96 wells contained a 10 micrograms of trypsin in 100 microliters of phosphate buffered saline along with a 10 micromolar peptide substrate for that enzyme. Under these conditions, trypsin cleaved the peptide substrate into two smaller peptides. Before the addition of the substrate, a different chemical from a previously selected chemical library was added to each of the 96 wells at varying concentrations to determine which compound, if any, would inhibit the conversion of substrate to products. The enzyme-substrate-inhibitor mixture was incubated in the 96 well microtiter plate for 1 hour at 37 degrees centigrade and 10 microliters of methanol was added to denature the enzyme and stop the reaction. The relative inhibition in each well was quantified by taking a mass spectrum of the reaction mixture and comparing the amount of products and substrate. In reactions in which the compound from the chemical library resulted in a high level of inhibition there was a large amount of substrate relative to products, whereas if little or no inhibition occurred there was a larger amount of products compared to substrate.

A linear array of 12 gas-tight 25 microliter syringes with blunt ended 22 gauge needles arranged with a 9 millimeter spacing (to match the wells of the 96 well microtiter plate) was used as the syringe array. A linear array of 0.7 millimeter interior diameter by 4 millimeter length columns, also with a 9 millimeter spacing was used as the chromatography column array 3 (see FIG. 1). A reversed phase column packing material with octadecyl surface chemistry on 5 micron silica beads was used for the chromatography media. A 50 micron internal diameter by 12 centimeter long metal tube was attached to the exit end of each chromatography column in the array 3 and used as the interface 4 between the chromatography column and the inlet 6 to the mass spectrometer. A 3000 V potential was be applied to all 12 tubes 4 at once by electrification of the metallic positioning jig to allow for electrospray ionization into the inlet 6 of the mass spectrometer.

The syringe array was cleaned in the syringe cleaning station by repeatedly aspirating methyl alcohol into syringes. Twenty microliters of 10% methyl alcohol and a 0.5 microliter air plug was aspirated into the syringes at the next station. The syringe bank was then moved over the microtiter plate and 1 microliter of the reaction mixture was aspirated into the syringe needle. The sample of 1 microliter was localized in the needle of the syringe and was separated from the 20 microliters of 10% methyl alcohol in the syringe barrel by the air plug. The syringes array was docked into the chromatography column array 3 through the compression fitting in the syringe port 1. The valves 2 between the syringe ports 1 and the columns in the array 3 were micro-check valves that allow for unidirectional flow from the syringes to the columns 3. A miniature diaphram valve 7 was situated between the pumping system and the tee at the head of each of the columns in the array. These valves 7 blocked fluid flow unless actuated by passing a current through them. The barrels of the array of syringes were depressed and the samples were loaded onto the columns 3. The substrate and products of the reaction adsorbed on to the column packing material and were retained. The 20 microliters of 10% methyl alcohol in the syringe barrel washed the salts (from the phosphate buffered saline) and precipitated enzyme through the column and the eluate was collected in a waste receptacle located below the mass spectrometer interface. The mass spectrometer was protected from the salts and contaminants since a voltage was not applied to the metal tubes 4 and as a result no electrospray ionization took place. The syringe array was removed from the compression fittings and the process cleaning the syringe array and of aspirating the next set of samples was begun.

A 3000 volt voltage was simultaneously applied to all of the 12 metal tubes 4 at the exit end of the chromatography columns that make up the mass spectrometer interface. The application of the voltage created a very small amount of liquid to be sprayed out of each tube 4 into the mass spectrometer, even without any positive pressure flow of fluid. This flow was comprised only of 10% methyl alcohol wash solvent since the samples of interest were still bound to the columns. The column array 3 was moved using the translation stage such that the first column in the array could be sprayed through an opening in a skimmer 9 into the inlet orifice 6 of the mass spectrometer. The diaphram valve 7 in this first column of the array was selectively opened with the application of a current and 80% methyl alcohol was applied to the column at a flow rate of 5 microliters per second from the pumping system 8. The check valve 2 between the column and the syringe port 1 blocked this flow from traveling up and out of the syringe port and forced it to travel through the chromatography column 3. The 80% methyl alcohol rapidly eluted the samples of interest (ie: substrate and/or products) from the column 3 and the samples were sprayed into the mass spectrometer inlet 6 through the electrospray interface 4. The valve 7 was kept open for 0.5 seconds, which was long enough for an acceptable mass spectrometer signal to be obtained. After 0.5 seconds the valve 7 was shut and the entire column array 3 was again moved with the translation stage such that the second column in the array 3 could spray into the mass spectrometer. The diaphram valve 7 of this second column in the array was opened, selectively delivering the 80% methyl alcohol elution solvent to that column. In this manner the samples within each of the 12 columns of the array 3 were analyzed by the mass spectrometer and the data was stored for later analysis. Once the final sample had been analyzed the voltage applied to the metal tubes 4 was terminated and samples were no longer sprayed into the inlet 6 of the mass spectrometer. The array of columns 3 was moved to the start position with the translation stage such that all of the electrospray needles 4 were excluded from spraying into the mass spectrometer.

To wash the columns in the array 3 all of the diaphram valves 7 were opened simultaneously and 80% methyl alcohol was delivered to the entire chromatography column array 3 at a flow rate of 20 microliters per second for 3 seconds. The column array 3 was then re-equilibrated by delivering 10% methyl alcohol for 2 seconds at 20 microliters per second. Total sample analysis time lasted for 0.5 seconds per each of the 12 samples for a total of 6 seconds while the washing and column regeneration took 5 seconds allowing for an average sample analysis time of 1 sample per second.

The mass spectrometer used was a triple quadrupole mass spectrometer programmed to operate in selective ion monitoring (SIM) mode such that only the masses of the substrate and the two product peptides were continually monitored. Mass spectrometer scans were obtained at the maximum rate of instrument performance, which was around 20 milliseconds per scan. A total of 20 scans were averaged per sample to obtain the final quantification. The low overall signal obtained in the scans taken during valve actuation during sample switching was used as a trigger to begin mass spectrometric analysis of the next sample. By taking the ratio of products to substrates for each sample the relative amount of inhibition that occurred in each well of the microtiter plate was determined.

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the appended claims.

What is claimed is:

1. A system for high throughput sample preparation and analysis using column chromatography, the system comprising:
    a) a plurality of ports, each port having both a port input that interfaces with a first fluid source and a port output;
    b) a fluidic circuit coupled to each port output and to a second fluid source, the fluidic circuit for controlling fluid flow from the plurality of ports and the second fluid source;
    c) a plurality of chromatography columns, each chromatography column coupled to the fluidic circuit;
    d) an interface to an analyzer that receives output from at least one of the plurality of chromatography columns; and
    e) a translation stage that allows for movement of the plurality of chromatography columns relative to the analyzer, such that sample output from one of the plurality of chromatography columns can be selectively presented to the analyzer.

2. A system according to claim 1, further comprising a plurality of syringes, each syringe for aspirating a sample to be analyzed and for acting as the first fluid source for one of the plurality of ports.

3. A system according to claim 2, wherein the plurality of syringes are in fixed positions relative to each other.

4. A system according to claim 3, wherein the plurality of syringes are positioned in a linear array with 9 millimeter spacing between each of the syringes.

5. A system according to claim 3, wherein the plurality of syringes interface with the plurality of ports in a parallel manner.

6. A system according to claim 2, further comprising a controller for controlling the plurality of syringes, the controller comprising at least one device from the group of devices consisting of a robot, a translational stage, and a computer.

7. A system according to claim 2, wherein each port includes a compression fitting for interfacing with one of the plurality of syringes.

8. A system according to claim 2, further comprising a washing station for cleaning the array of syringes.

9. A system according to claim 2, wherein the sample to be analyzed is located on a movable surface.

10. A system according to claim 9, wherein the movable surface is a fiber.

11. A system according to claim 9, wherein the movable surface is a laminate.

12. A system according to claim 9, wherein the movable surface is a belt.

13. A system according to claim 1, wherein the first fluid source includes a plurality of tubes, each tube for interfacing with one of the plurality of ports.

14. A system according to claim 1, wherein the fluidic circuit includes:
    a) a plurality of valves, each valve controlling fluid flow from the port output of one of the plurality of ports;
    b) a plurality of tee unions, each tee union coupled to one of the plurality of valves and at least one chromatography column.;
    c) a pump for pumping fluid from a second fluid source; and
    d) at least one selection valve for selectively coupling an output from the pump to at least one of the plurality of tee unions.

15. A system according to claim 14, wherein at least one of the plurality of valves is an actively controlled shutoff valve.

16. A system according to claim 14, wherein at least one of the plurality of valves is a passive check valve.

17. A system according to claim 1, wherein the interface includes a plurality of electrospray ionization sprayer tubes for interfacing with a mass spectrometer, each electrospray ionization sprayer tube coupled to one of the chromatography columns.

18. A system according to claim 1, wherein the plurality of chromatography columns are in fixed positions relative to each other.

19. A system according to claim 1, wherein the plurality of chromatography columns are positioned in a fixed linear array.

20. A method for high throughput sample preparation and analysis using column chromatography, the method comprising:
    a) interfacing a plurality of ports with a first fluid source, each port having both a port input coupled to the first fluid source and a port output;

b) controlling fluid flow from each port output and a second fluid source to a plurality of chromatography columns; and c) moving the plurality of chromatography columns relative to the analyzer, such that sample output from one of the plurality of chromatography columns can be selectively presented to the analyzer.

21. The method according to claim 20, further comprising:

a) aspirating samples into a plurality of syringes, and b) interfacing the plurality of syringes with the plurality of ports.

22. The method according to claim 21, further comprising controlling the syringes using at least one device from the group of devices consisting of a robot, a translational stage, and a computer.

23. The method according to claim 21, further comprising cleaning the syringes at a washing station prior to aspirating samples.

24. The method according to claim 20 wherein controlling fluid flow from each port output and a second fluid source to a plurality of chromatography columns includes:

a) controlling a plurality of valves so as to regulate fluid flow from the port output of each of the plurality of valves to a plurality of tee valves, each tee valve coupled to at least one of the plurality of chromatography columns; and b) selectively pumping fluid from the second fluid source to at least one of the plurality of tee valves.

25. The method according to claim 20, further comprising presenting sample from one of the plurality of chromatography columns to a mass spectrometer using an electrospray ionization sprayer tube.

26. The method according to claim 25, further comprising blocking undesired components from entering the mass spectrometer by removing the voltage applied to the electrospray ionization sprayer tube.

27. The method according to claim 25, further comprising blocking undesired components from entering the mass spectrometer by moving the electrospray ionization sprayer tube to a position in which the spray is physically blocked from entering the mass spectrometer.

28. The method according to claim 20, further comprising performing at least one operation from the group of operations consisting of optical interrogation and mass spectrometry.

29. The method according to claim 27, wherein optical interrogation includes at least one of flouresence spectrometry, Raman spectrometry, and UV absorption.

30. The method of claim 20, wherein controlling fluid flow includes delivering samples and wash from one of the plurality of ports to one of the plurality of chromatography columns in one substantially continuous action.

31. The method according to claim 20, wherein sample output can be selectively presented to the analyzer once every specified time period.

* * * * *

UNITED STATES PATENT AND TRADEMARK OFFICE
CERTIFICATE OF CORRECTION

| | |
|---|---|
| PATENT NO. | : 6,812,030 B2 |
| DATED | : November 2, 2004 |
| INVENTOR(S) | : Can C. Ozbal et al. |

It is certified that error appears in the above-identified patent and that said Letters Patent is hereby corrected as shown below:

The Title page, illustrative Fig. should be replaced with the attached figure.

Delete Drawing Sheet 2 of 4 and replace it with the attached drawing.

<u>Column 4,</u>
Lines 21-60, should read:
-- In accordance with one embodiment of the invention, fig. 2 is a schematic diagram of a system 9 for high throughput sample preparation and analysis in accordance with one embodiment of the invention. A plurality of ports 1 interface with a first fluid source. The first fluid source may include a plurality of syringes or tubes (hereinafter referred to as syringes). In various embodiments of the invention, the needles of the array of syringes are coupled to the array of chromatography columns 3 through compression fitting in ports 1. The compression fitting forms a fluid tight seal around the needles of the syringes.

Plurality of ports 1 are coupled to a fluidic circuit which controls fluid flow to the chromatography columns. In various embodiments of the invention, the fluidic circuit may include a valve 2 placed between each port 1 and chromatography column 3 in the array. Valve 2 can either be an actively controlled shutoff valve or a passive check valve that limits the flow only from the ports 1 to the columns 3. The fluidic circuit may also contain a tee union 4 between valve 1 and chromatography columns 3 of the array from which elution and wash buffers or solvents can be added to each of the chromatography columns 3 in the array from a pumping system 8. A second valve(s) 7 controls flow from the pumping system to a particular chromatography column(s). Valve(s) 7 may be, for example, a single selection valve or alternatively, may consist of a plurality of valves, with each valve 7 controlling flow to one of the plurality of chromatography columns 3.

UNITED STATES PATENT AND TRADEMARK OFFICE
CERTIFICATE OF CORRECTION

PATENT NO. : 6,812,030 B2
DATED : November 2, 2004
INVENTOR(S) : Can C. Ozbal et al.

It is certified that error appears in the above-identified patent and that said Letters Patent is hereby corrected as shown below:

Column 4 (cont'd),
The eluate of each of the columns 3 in the array is channeled into an interface 4 for an analyzer. The analyzer may include, but is not limited to, optical interrogation and mass spectrometry. Types of optical interrogation that may be performed include fluorescence spectrometry, Raman spectrometry, or UV absorption. The interface 4 may include a simple tube attached to each column 3 so as to direct the fluid to the analyzer, or the interface may be more complex. For example, the eluate may be channeled into a thin metal tube 9 onto which a voltage can be applied for direct atmospheric pressure electrospray ionization for use with a mass spectrometer. --.

Signed and Sealed this

Seventeenth Day of January, 2006

JON W. DUDAS
*Director of the United States Patent and Trademark Office*